United States Patent [19]

Redmore

[11] Patent Number: 4,579,956

[45] Date of Patent: Apr. 1, 1986

[54] AMINO-PHOSPHONATES

[75] Inventor: Derek Redmore, Ballwin, Mo.

[73] Assignee: Petrolite Corporation, St. Louis, Mo.

[21] Appl. No.: 953,240

[22] Filed: Oct. 20, 1978

Related U.S. Application Data

[63] Continuation of Ser. No. 513,822, Oct. 10, 1974, abandoned, which is a continuation of Ser. No. 115,888, Feb. 16, 1971, abandoned.

[51] Int. Cl.$^4$ ............................ C07F 9/65; C07F 9/58; C07F 9/40
[52] U.S. Cl. .................................... 548/413; 544/157; 544/88; 544/63; 546/22; 252/609; 252/82; 252/389 A
[58] Field of Search ................... 546/22; 260/326.5 A, 260/958; 544/157

[56] References Cited

U.S. PATENT DOCUMENTS

| | | | |
|---|---|---|---|
| 2,460,043 | 1/1949 | Teeters | 260/958 |
| 2,635,112 | 4/1953 | Fields | 260/945 |
| 2,795,609 | 6/1957 | Jensen | 260/958 |
| 2,847,442 | 8/1958 | Sallman | 260/945 |
| 3,155,708 | 11/1964 | Chupp | 260/958 |
| 3,352,948 | 11/1967 | Kawahara et al. | 260/945 |

OTHER PUBLICATIONS

Khamitov et al, Dokl. Akad. Nauk, SSSR, vol. 172(5), pp. 1099–1101, (1967).
Fieser et al, Organic Chemistry, pp. 49–50 (1944).
Hawley, The Condensed Chemical Dictionary, 8th Ed., p. 252.

Primary Examiner—Mark L. Berch
Attorney, Agent, or Firm—Sidney B. Ring; Leon J. Bercovitz

[57] ABSTRACT

Amino-phosphonates are prepared by reacting an enamine with a phosphite ester, for example, according to the equation

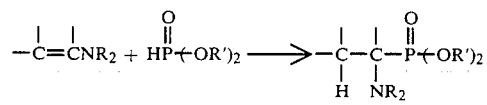

where OR' is an alcohol moiety and NR$_2$ is an amino moiety, both R and R' being preferably hydrocarbon such as alkyl or R$_2$ is part of a ring structure. These compounds have many uses, for example, as corrosion inhibitors, scale inhibitors, fuel stabilizers, etc. In addition, amino-phosphonates can be converted to alpha, beta - unsaturated phosphonates according to the equation

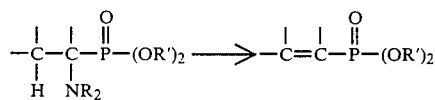

which are useful in forming flame retardant polymers and copolymers.

5 Claims, No Drawings

AMINO-PHOSPHONATES

This is a continuation of application Ser. No. 513,822, filed Oct. 10, 1974, now abandoned, which was a continuation of application Ser. No. 115,888, filed Feb. 16, 1971, now abandoned.

This invention relates to amino-phosphonates, their preparation and uses. This invention also relates to the conversion of the amino-phosphonates to unsaturated phosphonates.

"Enamines" is a term employed for an alpha, beta-unsaturated amine, for example of the general formula

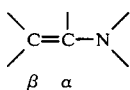

These include both linear and cyclic enamines. Enamines are prepared by a wide variety of procedures, such as from reaction of carbonyl compounds such as ketones and aldehydes, with amines, according to the equation:

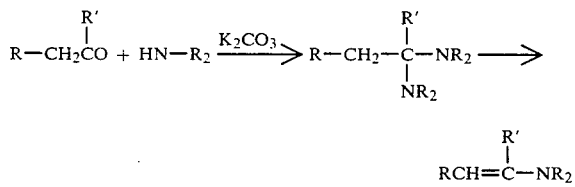

where R's, which may be the same or different, are for example, hydrocarbon groups, and R' is a hydrocarbon group or hydrogen.

Specific reactions are as follows:

The reaction of an aldehyde

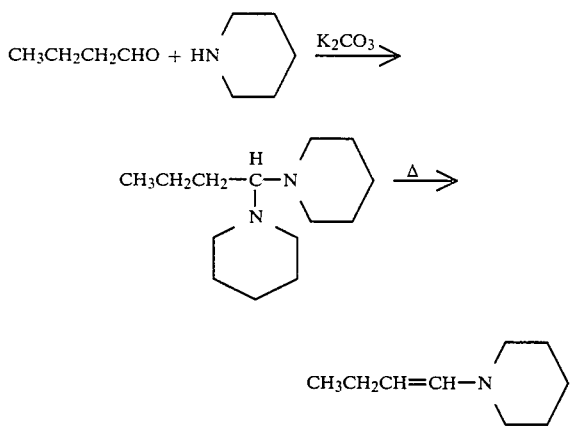

The reaction of a ketone

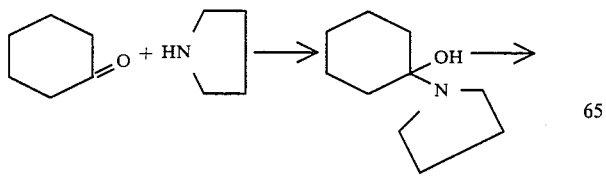

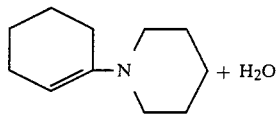

Enamines also are formed by alkylation:

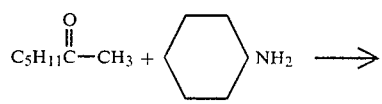

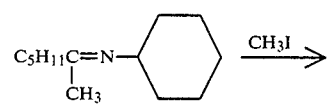

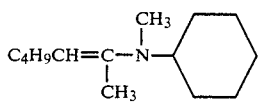

Enamines may also be prepared by other procedures, for example, by the procedures described in "Advances in Organic Chemistry", Volume 4, Interscience Publishers, 1963, Enamines, pages 1–114, which is incorporated herein by reference.

Enamines are reacted with phosphite esters according to the following reaction:

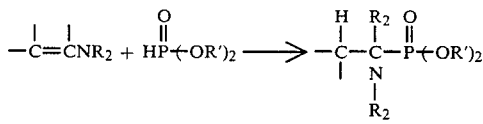

where R is an alcohol moiety such as hydrocarbon, i.e., alkyl, cycloalkyl, aryl, alkaryl, aralkyl, etc., and R' is also hydrocarbon such as alkyl, part of a ring structure, etc.

In general, the reactants are heated, for example, at 100° C.±25°, for sufficient time to yield the desired products, such as from 1 to 5 hours. The ratio of reactants employed are stoichiometric, i.e., 1 mole of enamine to 1 mole of phosphite.

The following are illustrative examples of the reaction of enamines with phosphites to form the products of this invention.

EXAMPLE 1

A mixture of 1-pyrrolidinocyclohexene (15.1 g; 0.1 mole) and diethyl phosphite (13.8 g; 0.1 mole) was heated for 2 hours on a steam bath. The resulting liquid showed no absorption in the infrared for C=C or P-H. Distillation yielded pure diethyl 1-pyrrolidinocyclohexane-1-phosphonate, bp 80°–85°/0.1 mm.

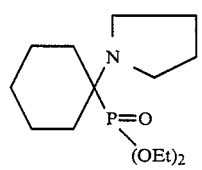

EXAMPLE 2

A mixture of diethyl phosphite (13.8 g; 0.1 mole) and 1-morpholinocyclopenetene (15.3 g; 0.1 mole) was heated at 100° for 2 hours with exclusion of moisture. The resulting oil showed no C═C or P-H absorption in the infrared. Distillation yielded pure diethyl 1-morpholinocyclopentane-1-phosphonate, bp 85°-90°/0.1 mm.

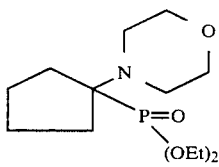

EXAMPLE 3

To 1-morpholinocyclohexene (21.5 g; 0.13 mol) was added diphenyl phosphite (30 g; 0.13 mol) drop-wise during 20 minutes. The mixture which began to deposit a solid was heated at 100° for 30 minutes following the addition. After cooling, the resulting solid was recrystallized from benzene/hexane to yield pure diphenyl 1-morpholinocyclohexane-1-phosphonate, 37 g (70%), mp 103°-6°. NMR and IR spectra support the structure. Analysis: Calculated for $C_{22}H_{28}NO_4P$; N, 3.49%; P, 7.73%. Found: N, 3.40% P, 7.70%.

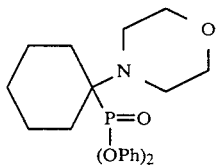

EXAMPLE 4

To the morpholine enamine of isobutyraldehyde (21.5 g; 0.15 mol) was added diphenyl phosphite (35.8 g; 0.15) drop-wise during 30 minutes with cooling to keep the reaction temperature below 60°. After stirring 1 hour, ambient temperature infrared indicated complete reaction by the absence of C═C and P-H absorption. NMR was fully consistent with the following structure:

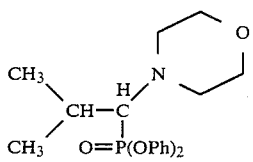

EXAMPLE 5

To the morpholine enamine of isobutyraldehyde (33.5 g; 0.24 mol) was added diethyl phosphite and the resulting mixture heated at 100° for 2 hours. Distillation of the resulting liquid gave the pure phosphonate bp 98°-100°/0.1 mm. Analysis: Calculated for $C_{12}H_{26}NO_4P$; N, 5.02%; P, 11.10%. Found: N, 4.80% P, 11.07%. Structure of product is:

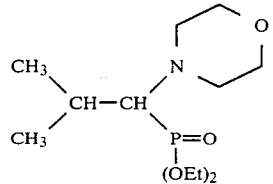

EXAMPLE 6

To the pyrrolidine enamine of α-tetralone (7.5 g; 0.038 mol) dissolved in benzene (30 ml) was added diphenyl phosphite (8.8 g; 0.038 mol) in benzene (10 ml) during 30 minutes. After the addition the mixture was heated at 80° for 1 hour. After evaporation of the solvent a quantitative yield of diphenyl 1-pyrrolidino tetralin-1-phosphonate was obtained. The structure is:

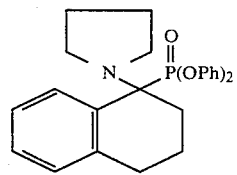

EXAMPLE 7

This example illustrates the reaction using an aryl ketone.

To the piperidine enamine of acetophenone (8.9 g; 0.048 mol) dissolved in benzene (15 ml) was added dephenyl phosphite (11.1 g; 0.048 mol) in benzene (15 ml). The addition was slightly exothermic and the reaction was completed by heating at 80° for 2 hours. The infrared and NMR spectra were consistent with the following structure:

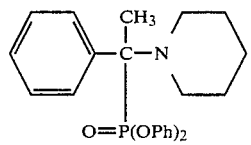

The following are illustrative examples of enamines that can be reacted with phosphites to form the products of this invention according to above procedures; to yield corresponding products with both diethyl phosphite and diphenyl phosphite.

As is evident, the compounds shown have a nitrogen atom which is part of a heterocyclic ring containing 5 or 6 members, the 5 membered heterocylic rings containing nitrogen as the sole hetero atom and the 6 membered heterocyclic rings containing as hetero atoms said nitrogen atoms and not more than one oxygen atom.

TABLE A

| Ex. | |
|---|---|
| 8. | 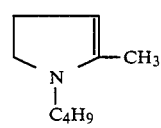 |

TABLE A-continued
| Ex. | |
|---|---|
| 9. | 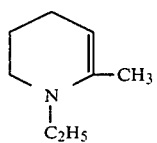 |
| 10. | 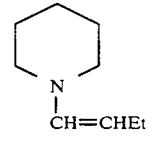 |
| 11. | 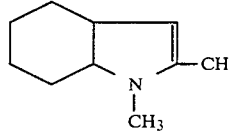 |
| 12. | 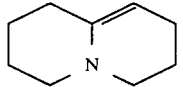 |
| 13. | 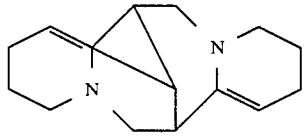 |
| 14. | 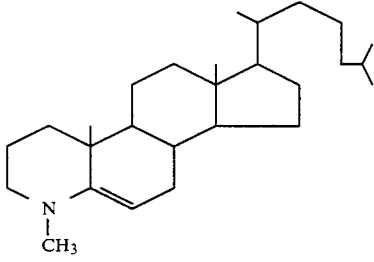 |
| 15. | 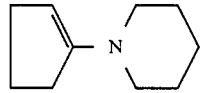 |
| 16. | 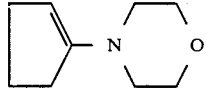 |
| 17. | 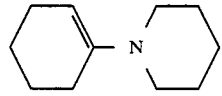 |
| 18. | 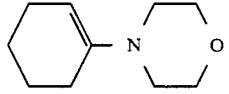 |
TABLE A-continued
| Ex. | |
|---|---|
| 19. | 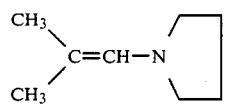 |
| 20. | 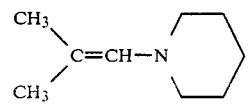 |
| 21. | 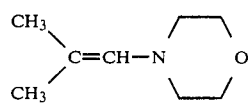 |
| 22. | 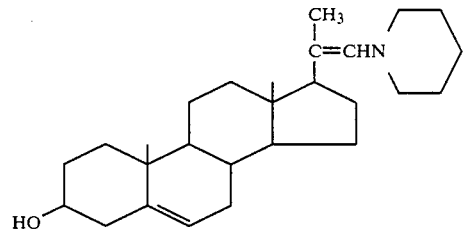 |
| 23. | 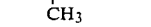 |
| 24. | 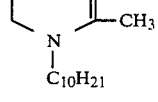 |
| 25. | 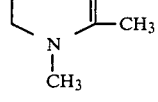 |
| 26. | 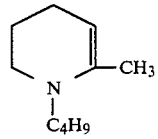 |
| 27. | 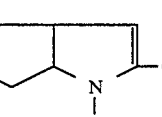 |
| 28. | 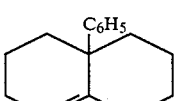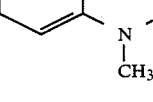 |

TABLE A-continued

| Ex. | |
|---|---|
| 29. | (structure: bicyclic diene with two N-containing rings, CH₃ groups) |
| 30. | (steroid-like structure with N–C₂H₅ group) |

These products are also convertable to unsaturated phosphenates according to the following reaction:

$$-\underset{\underset{NR_2}{|}}{\overset{\overset{H}{|}}{C}}-\underset{|}{C}-\overset{\overset{O}{\|}}{P}(OR')_2 \longrightarrow -\underset{|}{C}=\underset{|}{C}-\overset{\overset{O}{\|}}{P}(OR')_2.$$

The enamine-phosphite reaction products can be employed as corrosion inhibitors, scale inhibitors, fuel additives, lube additives, biocides, i.e., bactericides, algicides, etc., antistatic agents for textiles, plastics, etc.

The compositions of this invention may be described as amino-phosphonates characterized by a phosphonate moiety such as a phosphonate ester group and a secondary amino group attached to the same carbon atom i.e., esters of phosphonic acid having the nitrogen atom of an amino group attached to the carbon atom alpha to the phosphonate moiety. These compounds are referred to herein as esters of α-amino phosphonic acids. In most instances the secondary amino group is cyclic. The common carbon to which both the phosphonate and the amino group are attached may exist in a linear form or as part of a cyclic group. Thus the compound may be presented by the formula $$C\underset{\underset{P(OR)_2}{\overset{\|}{\underset{O}{}}}}{\overset{N}{\diagup}}$$

where N is a cyclic amino group, for example a 6 member nitrogen-containing ring such as a piperidine ring, a 5 member nitrogen-containing ring such as pyrrolidine, a 6 member nitrogen- and oxygen-containing ring such as morpholine, etc., and C is an alicyclic ring wherein a carbon atom beta to the phosphonate moiety has at least one hydrogen atom bonded thereto, which alicyclic ring may be a 5 member ring such as cyclopentane or a 6 member ring, or a bicyclic carbon ring system containing such an alicyclic ring, such as tetralin, etc. Where the composition contains a common carbon which is part of a linear configuration the formula may be presented as $$R-\underset{\underset{\overset{\|}{O}}{\overset{|}{P}-(OR')_2}}{\overset{\overset{R''}{|}}{C}}$$

where R'' is a hydrogen or a substituted group such as alkyl, aryl, alkaryl, aralkyl, etc., and R is alkyl, aryl, alkaryl, aralkyl, etc., and R' is alkyl, cycloalkyl, aryl, alkaryl or aralkyl, etc. Representative illustrations have been presented herein.

As is quite evident, new enamines will be constantly developed which could be useful in this invention. It is, therefore, not only impossible to attempt a comprehensive catalogue of such compositions, but to attempt to describe the invention in its broader aspects in terms of specific chemical names used would be too voluminous and unnecessary since one skilled in the art could by following the description of the invention herein select a useful enamine to be reacted. This invention lies in the reaction of suitable enamines with phosphites to yield the desired products. To precisely define each specific useful enamine and phosphite in light of the present disclosure would merely call for knowledge within the skill of the art in a manner analogous to a mechanical engineer who prescribes in the construction of a machine the proper materials and the proper dimensions thereof. From the description in this specification and with the knowledge of a chemist, one will know or deduce with confidence the applicability of specific suitable enamines. I can obviously assume that no one will wish to use a useless enamine or a useless phosphite nor will be misled because it is possible to misapply the teachings of the present disclosure to do so. Thus, any enamine and phosphite that can react as stated herein can be employed.

I claim:

1. An ester of an α-amino phosphonic acid wherein the alpha carbon atom is part of an alicyclic ring which is part of a bicyclic carbon ring system and wherein a carbon atom in said alicyclic ring beta to the phosphonate moiety has at least one hydrogen atom bonded thereto; and the nitrogen atom of the amino moiety is part of a heterocyclic ring containing 5 or 6 members, said 5 membered heterocyclic rings containing only said nitrogen atom as hetero atoms and said 6 membered heterocyclic rings containing as hetero atoms only said nitrogen atom and not more than one oxygen atom.

2. An amino-phosphonate of claim 1 of the formula $$C\underset{\underset{P(OR)_2}{\overset{\|}{\underset{O}{}}}}{\overset{N}{\diagup}}$$

wherein N is a cyclic amino group which is a heterocyclic ring as defined in claim 1, C is a bicyclic carbocyclic group containing an alicyclic ring as defined in claim 1 and R is hydrocarbon.

3. An amino-phosphonate of claim 2 where N is (pyrrolidine ring), N (piperidine ring) or N O (morpholine ring), and C is

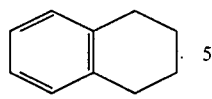
4. An amino-phosphonate of claim 2 where R is alkyl or phenyl.
5. The amino-phosphonate of claim 4 where the formula is
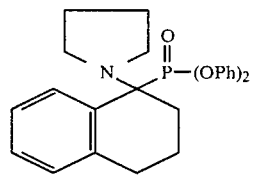
wherein Ph is phenyl.
* * * * *